United States Patent [19]

Hasspacher

[11] 4,351,838
[45] Sep. 28, 1982

[54] INDANE DERIVATIVES, PROCESS FOR THEIR PREPARATION, THEIR USE AS PHARMACEUTICALS AND PHARMACEUTICAL COMPOSITIONS CONTAINING SAID DERIVATIVES

[75] Inventor: Klaus Hasspacher, Riehen, Switzerland

[73] Assignee: Sandoz Ltd., Basel, Switzerland

[21] Appl. No.: 233,707

[22] Filed: Feb. 12, 1981

[30] Foreign Application Priority Data

Feb. 13, 1980 [CH] Switzerland .......................... 1170/80

[51] Int. Cl.³ .................. A61K 31/445; C07D 211/06
[52] U.S. Cl. ..................................... 424/267; 546/205
[58] Field of Search ........................ 546/205; 424/267

[56] References Cited

U.S. PATENT DOCUMENTS

| | | | |
|---|---|---|---|
| 2,916,490 | 12/1959 | Schenck | 546/205 |
| 3,328,411 | 6/1967 | Borck | 546/205 |
| 3,822,310 | 7/1974 | Shen et al. | 546/205 |
| 4,172,093 | 10/1979 | Göransson-Dahlander | 546/205 |
| 4,251,655 | 2/1981 | Scott et al. | 546/205 |

FOREIGN PATENT DOCUMENTS 57713 7/1969 Poland .

OTHER PUBLICATIONS

Chem. Abstracts 72: 100361y, (1970).
Borkowska et al., Dissert Pharm. Pharmacol., 1972, XXIV, 321.

*Primary Examiner*—Ethel G. Love
*Attorney, Agent, or Firm*—Gerald D. Sharkin; Robert S. Honor

[57] ABSTRACT

The invention provides compounds of formula

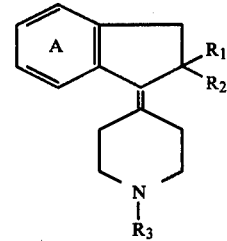

wherein $R_1$ and $R_2$ are alkyl, $R_3$ is hydrogen, alkyl, alkenyl, phenylalkyl or a group —$(CH_2—CH_2—O)_n—R_4$ in which n is 1 to 3 and $R_4$ is hydrogen or an acid residue, and the ring A is unsubstituted or substituted, with the proviso that when $R_3$ is methyl the ring A is substituted. The compounds are useful in the treatment and prophylaxis of allergic conditions.

12 Claims, No Drawings

INDANE DERIVATIVES, PROCESS FOR THEIR PREPARATION, THEIR USE AS PHARMACEUTICALS AND PHARMACEUTICAL COMPOSITIONS CONTAINING SAID DERIVATIVES

The present invention relates to new indane derivatives, their preparation, their use as pharmaceuticals and pharmaceutical compositions containing them.

More particularly the invention provides an indane derivative of formula I

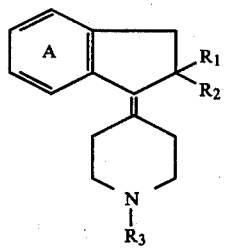

(I)

wherein $R_1$ and $R_2$, independently, are $C_{1-4}$alkyl, $R_3$ is hydrogen; $C_{1-4}$alkyl; $C_{3-5}$alkenyl; $C_{7-10}$phenylalkyl optionally substituted in the phenyl ring by halogen, $C_{1-4}$alkyl or $C_{1-4}$alkoxy; or a group of formula (a)

$$-(CH_2-CH_2-O)_n-R_4 \quad (a)$$

wherein n is an integer of from 1 to 3 and $R_4$ is hydrogen or a physiologically-acceptable and -hydrolysable acid residue, and the ring A is unsubstituted or substituted, with the proviso that when $R_3$ is methyl the ring A is substituted, as well as the salts thereof.

In the present specification and claims halogen means fluorine, chlorine or bromine.

Alkyl and alkoxy radicals in formula I may be branched or straight chain and preferably contain 1 or 2 carbon atoms.

$R_1$ and $R_2$ are preferably the same. $R_1$ and $R_2$ are especially $C_{1-2}$alkyl, more especially methyl.

When $R_3$ is alkyl, this is preferably $C_{1-2}$alkyl or, more preferably, methyl. When $R_3$ is alkenyl this may be branched or straight chain and is especially allyl.

When $R_3$ is phenylalkyl this is preferably benzyl. When the phenyl ring of a phenylalkyl radical $R_3$ is substituted, there are conveniently 1 or 2 substituents. Preferred substituents are halogen, in particular fluorine and bromine, $C_{1-4}$alkyl, in particular methyl, and $C_{1-4}$alkoxy, in particular methoxy. Preferably the phenyl ring is unsubstituted.

In the group of formula (a), n may be 1, 2 or 3. Preferably n is 1 or 2.

By the term "physiologically-hydrolysable and -acceptable acid residue" is meant an acid residue which is removable by hydrolysis under physiological conditions and which is itself physiologically acceptable, i.e. non toxic. $R_4$ in formula (a) may accordingly represent e.g. a carboxylic acyl residue, e.g. acetyl or benzoyl. Preferably $R_4$ is hydrogen.

Ring A may optionally be substituted, e.g. di- or, preferably, mono-substituted. Preferably ring A is unsubstituted or is mono-substituted. Preferred substituents are fluorine, chlorine, $C_{1-4}$alkyl, in particular methyl, and $C_{1-4}$alkoxy, in particular methoxy.

In a preferred group of compounds of formula I, $R_3$ is hydrogen or alkyl, most preferably alkyl, and ring A is substituted.

In a second preferred group of compounds of formula I, $R_3$ is a group of formula (a) and ring A is unsubstituted or substituted.

A group of compounds in accordance with the invention, are those of formula I wherein $R_1$ and $R_2$, independently, are $C_{1-4}$alkyl, $R_3$ is hydrogen, $C_{1-4}$alkyl, $C_{3-5}$alkenyl, $C_{7-10}$phenylalkyl optionally substituted in the phenyl ring by 1 or 2 substituents selected from fluorine, chlorine, methyl and methoxy, or a group of formula (a) wherein $R_4$ is hydrogen, and wherein the ring A is optionally monosubstituted by fluorine, chlorine, $C_{1-4}$alkyl or $C_{1-4}$alkoxy, with the proviso that when $R_3$ is methyl, the ring A is substituted.

The present invention further provides a process for the production of a compound of formula I as defined above, which process comprises (a) preparing a compound of formula I wherein $R_3$ is $C_{1-4}$alkyl or $C_{7-10}$phenylalkyl optionally substituted in the phenyl ring by halogen, $C_{1-4}$alkyl or $C_{1-4}$alkoxy, by dehydrating a compound of formula II

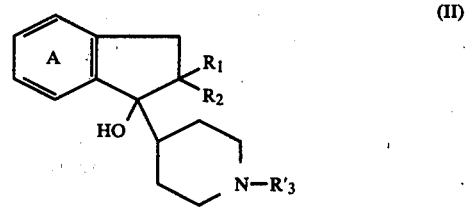

(II)

in which $R_1$ and $R_2$ are as defined above, the ring A is substituted or unsubstituted and $R_3'$ is $C_{1-4}$alkyl or $C_{7-10}$phenylalkyl optionally substituted in the phenyl ring by halogen, $C_{1-4}$alkyl or $C_{1-4}$alkoxy; or (b) preparing a compound of formula I wherein $R_3$ is hydrogen, by hydrolysing a compound of formula III

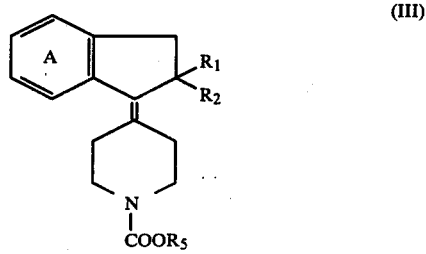

(III)

in which $R_1$ and $R_2$ are as defined above, the ring A is substituted or unsubstituted and $R_5$ is $C_{1-4}$alkyl; or (c) preparing a compound of formula I wherein $R_3$ is other than hydrogen, by reacting a compound of formula IV

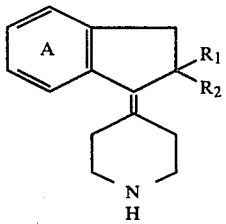

(IV)

in which $R_1$ and $R_2$ are as defined above and the ring A is substituted or unsubstituted, with a compound of formula V $$R_6\text{—}X \qquad (V)$$

in which $R_6$ has the meaning given for $R_3$ above excluding hydrogen, and X is the acid residue of a reactive ester; or (d) preparing a compound of formula I wherein $R_3$ is a group of formula (a) in which $R_4$ is a physiologically-hydrolysable and -acceptable acid residue, by esterifying a compound of formula I in which $R_3$ is a group of formula (a) wherein $R_4$ is hydrogen; or (e) preparing a compound of formula I wherein $R_3$ is a group of formula (a) in which $R_4$ is hydrogen, by hydrolyzing a compound of formula I wherein $R_3$ is a group of formula (a) in which $R_4$ is an acid residue, and when required recovering the compound of formula I in free base form or in salt form.

The dehydratation according to process (a), may be effected in conventional manner, for example in the presence of a mineral acid, e.g. hydrochloric acid or sulfuric acid in an aqueous or alcoholic medium, or in glacial acetic acid, at temperatures from 50° to 100° C., for example at the boiling temperature of the reaction mixture.

The hydrolysis according to process (b), may be effected in accordance with conventional means for hydrolysing carbamates to produce secondary amines, for example using acids, such as mineral acids e.g. hydrochloric acid, or using bases such as alkaline hydroxides e.g. potassium or sodium hydroxide. The reaction may be carried out for example in an inert solvent, e.g. a lower alcohol, preferably at the boiling temperature of the reaction mixture.

The alkylation according to process (c), may be effected in conventional manner for the alkylation of secondary amines. The reaction is conveniently carried out in an inert organic solvent, preferably in the presence of a basic condensation agent, e.g. sodium carbonate, at temperatures from room temperature to about 100° C. In the compounds of formula V, X is for example a halogen atom such as chlorine, bromine or iodine, or the acid residue of an organic sulfonic acid, e.g. an alkylsulfonyloxy radical such as methylsulfonyloxy, or an arylsulfonyloxy radical such as phenylsulfonyloxy or p-toluenesulfonyloxy.

The esterification according to process (d) may be effected in conventional manner, e.g. by reaction with an appropriate physiologically acceptable acid or a reactive functional derivative thereof.

The hydrolysis according to process (e) may also be effected by known methods, e.g. in an alkaline medium.

The resulting compounds of the invention may be isolated from the reaction mixture in free base or salt form, and purified in known manner. Free base forms may be converted e.g. into acid addition salt forms in conventional manner and vice versa. Suitable acids for salt formation are hydrochloric acid and maleic acid.

The starting materials of formula II may be produced by condensing compounds of formula VI

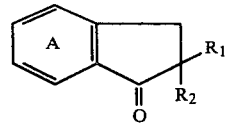

(VI)

wherein $R_1$, $R_2$ and the ring A are as defined above, with compounds of formula VII

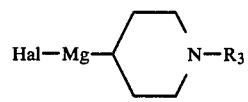

(VII)

in which $R_3'$ is as defined above and "Hal" is a halogen atom, e.g. a chlorine atom, in accordance with the Grignard method and hydrolysing the obtained reaction product.

The starting materials of formula III may be obtained by reacting a compound of formula I in which $R_3$ is methyl, with a compound of formula VIII $$\text{Hal—COOR}_5 \qquad (VIII)$$

in which "Hal" and $R_5$ are as defined above. The reaction is preferably carried out in an inert solvent, for example an aromatic hydrocarbon, e.g. toluene, and at the boiling temperature of the reaction mixture.

The products of the above reactions may be isolated and purified in known manner.

Insofar as the preparation of any of the starting materials defined above is not particularly described, such preparation may be effected in conventional manner or analogously to known methods. Compounds of formula VI are described for example in Elsevier's Encyclopaedia of Organic Chemistry, Vol 12A, series III, Elsevier Publishing Company Inc. New York 1948.

In the following Examples all temperatures are given in degrees Celsius and are uncorrected.

EXAMPLE 1

4-(6-chloro-2,2-dimethyl-indane-1-ylidene)-1-methyl-piperidine hydrochloride (a) A Grignard reagent is prepared from 14.0 g 4-chloro-N-methylpiperidine and 2.6 g magnesium in 200 ml boiling tetrahydrofuran. After cooling, a solution of 10.0 g 6-chloro-2,2-dimethyl-indanone in 50 ml tetrahydrofuran is added dropwise at 5°–10°, and the reaction mixture is refluxed for 6 hours. After cooling, a 10% aqueous solution of ammonium chloride is added and the mixture is extracted with toluene. The toluene phase is dried and evaporated, to give 6-chloro-2,2-dimethyl-1-(1-methyl-4-piperidinyl)indan-1-ol (m.p. 181°–182°).

(b) 8.0 g of the compound obtained under (a) are refluxed for 3 hours in 100 ml hydrochloric acid in ethanol. The solution is then evaporated and the residue is recrystallized from ethanol, to give the title compound (m.p. 262°–265°).

The following compounds are obtained in analogous manner from the appropriate starting materials:

(i) 4-(4,6-dichloro-2,2-dimethyl-indane-1-ylidene)-1-methyl-piperidine; and
(ii) bis[4-(2,2,4-trimethyl-indane-1-ylidene)-1-methyl-piperidine]naphtalene-1,5-disulphonate; m.p. 250°–253°.

EXAMPLE 2

4-(2,2-dimethylindane-1-ylidene)piperidine 43 g 4-(2,2-dimethylindane-1-ylidene)-1-methyl-piperidine and 65 g ethyl chloroformate in 800 ml toluene are refluxed for 3 hours. After cooling, the solution is washed with 1 N hydrochloric acid and water, dried over magnesium sulfate and the toluene distilled off. The oily residue is then refluxed for 6 hours in 90 ml n-butanol and 9 g potassium hydroxide. The reaction mixture is cooled, filtered, diluted with ether and shaken out with water until neutral. The organic phase is then dried over magnesium sulfate and evaporated, to give the title compound as the hydrogenofumarate: m.p. 200°–202°.

EXAMPLE 3

2-{2-{2-[4-(2,2,-dimethyl-indane-1-ylidene)piperidine-yl]ethoxy}ethoxy}ethanol 2.5 g 4-(2,2-dimethyl-indane-1-ylidene)-piperidine, 1.95 g triethyleneglycol-monochlorhydrin and 2 g sodium carbonate in 50 ml methylisobutylketone are refluxed with stirring for 12 hours. After cooling, the reaction mixture is filtered and the filtrate evaporated. The residue is dissolved in ether, the solution washed two times with a little cold water, dried over sodium sulfate, filtered and evaporated, to give the title compound as a viscous oil. The neutral oxalate melts at 82°–85°.

Proceding analogously, bis {2-{2-[4-(2,2-dimethyl-indane-1-ylidene)-piperidine-1-yl]ethoxy}ethanol}oxalate is obtained from the appropriate starting materials (m.p. 108°–111°).

The compounds of formula I possess pharmacological activity. In particular, the compounds possess anti-anaphylactic activity, and are therefore useful in the treatment and prophylaxis of allergic conditions, such as allergic asthma, allergic disorders and exersice-induced asthma, as indicated in the passive cutaneous anaphylaxis (PCA) test in the rat after administration of the compounds at doses from about 0.1 to about 10 mg/kg per os.

The method employed is based on those described by Mota, Immunology 7, 681 (1964) and Stofland and Share, J. Physiol. Pharmacol. 52,1114 (1974). Female rats (180–200 g) are sensitized by subcutaneous administration of 1 mg of ovalbumin and 200 mg aluminium hydroxid, dissolved in 1 ml of physiological saline solution and intraperitoneal administration of 0.5 ml of Haemophilus pertussis vaccine (Schweizerisches Serum- und Impf- institut, Bern, Switzerland; $4 \times 10^{10}$ organism/ml). Fourteen day later, the animals are decapited, the blood centrifuged and the serum (anti-ovalbumin serum) collected and deep frozen.

The diluted anti-ovalbumin serum is injected intradermally (0.1 ml per injection site) at three sites on the backs of untreated, female rats. Twenty-four hours after the passive sensitisation, the rats receive either solvent or the test compound i.v. in a tail-vein or per os. Immediately afterwards or, in the case of p.o. administration, 60 minutes later, the animals receive an intravenous injection of 1 ml of antigen. The antigen (5 mg/ml) is dissolved in a 0.25% solution of Evans blue dye in physiological saline. In the controls this injection elicits a cutaneous anaphylactic reaction, the intensity of which is proportional to the distance to which the dye diffuses into the tissue surrounding the four sensitisation sites. Thirty minutes later, the rats are killed by $CO_2$ inhalation and the diameter in mm of the blue spot at each injection site measured. The drug dose decreasing the diameter of the blue area by 50% compared with solvent pretreated control rats (ED50), is obtained from the regression line. The dose-effect correlation is tested for statistical significance.

For the above-mentioned use, the dosage will, of course, vary depending on the compound employed, mode of administration and therapy desired. However, in general, satisfactory results are obtained on administration at a daily dosage of from about 0.01 to about 10 mg/kg of animal body weight, conveniently given in divided doses 2 to 4 times a day or in sustained release form. For the larger mammal, the total daily dosage is in the range of from about 1 to about 100 mg, and dosage forms suitable for oral administration comprise from about 0.25 to about 50 mg of the compounds admixed with a solid or liquid pharmaceutical carrier or diluent.

The compound may be administered in free form or e.g. in pharmaceutically acceptable acid addition salt form. Such salt forms possess the same order of activity as the free form and are readily prepared in conventional manner. Examples of suitable acids for the formation of salts include hydrochlorid acid, oxalic acid, fumaric acid and naphthalene-1,5-disulfonic acid.

In accordance with the foregoing the present invention also provides:

(i) A compound of formula I as hereinbefore defined, in free base or in pharmaceutically acceptable salt form, for use as a pharmaceutical. e.g. for use in the treatment or prophylaxis of allergic conditions, in particular allergic asthma, allergic disorders and exercise-induced asthma; as well as (ii) a pharmaceutical composition comprising a compound of formula I as hereinbefore defined, in free base or in pharmaceutically acceptable salt form together with a pharmaceutically acceptable diluent or carrier therefor.

What we claim is:

1. A compound of formula I

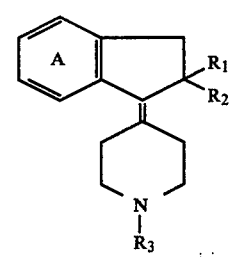

(I)

wherein
$R_1$ and $R_2$, independently, are $C_{1-4}$alkyl,
$R_3$ is hydrogen; $C_{1-4}$alkyl; $C_{3-5}$alkenyl; $C_{7-10}$phenylalkyl optionally substituted in the phenyl ring by halogen, $C_{1-4}$alkyl or $C_{1-4}$alkoxy; or a group of formula (a)

$$-(CH_2-CH_2-O)_n-R_4 \qquad (a)$$

wherein n is an integer of from 1 to 3 and $R_4$ is hydrogen or a non-toxic acid residue which is removable by hydrolysis under physiological conditions, and the ring A is mono-or-di-substituted by fluoro, chloro or $C_{1-4}$alkoxy groups, in free base or in pharmaceutically acceptable acid addition salt form.

2. A compound according to claim 1 wherein $R_3$ is hydrogen or $C_{1-4}$alkyl.

3. A compound according to claim 2 wherein $R_3$ is methyl.

4. A compound according to claim 1 wherein $R_3$ is a group of formula (a).

5. A compound according to claim 1 wherein, when $R_3$ is a group of formula (a), $R_4$ is hydrogen.

6. A compound according to claim 1 wherein ring A is substituted by chloro.

7. A compound according to claim 1 which is 4-(6-chloro-2,2-dimethyl-indane-1-ylidene)-1-methyl-piperidine in free base or salt form.

8. A compound according to claim 1 which is 4-(4,6-dichloro-2,2-dimethyl-indane-1-ylidene)-1-methyl-piperidine in free base or salt form.

9. A compound according to claim 1 which is 2-{2-{2-[4-(2,2-dimethyl-indane-1-ylidene)-piperidine-1-yl]-ethoxy}ethoxy}ethanol in free base or salt form.

10. A compound according to claim 1 which is 2-{2-[4-(2,2-dimethyl-indane-1-ylidene)-piperidine-1-yl]-ethoxy}ethanol in free base or salt form.

11. A method for the treatment or prophylaxis of asthma in a subject in need of such treatment, which method comprises administering to said subject an anti-asthma effective amount of a compound according to claim 1 in free base or pharmaceutically acceptable acid addition salt form.

12. A pharmaceutical composition for the treatment of asthma comprising an anti-asthma effective amount of a compound according to claim 1 in free base or pharmaceutically acceptable acid addition salt form, together with a pharmaceutically acceptable diluent or carrier therefor.

* * * * *